United States Patent [19]
Jakobsson et al.

[11] Patent Number: 6,102,922
[45] Date of Patent: Aug. 15, 2000

[54] SURGICAL METHOD AND DEVICE FOR REDUCING THE FOOD INTAKE OF PATIENT

[75] Inventors: Arne Jakobsson, Antibes, France; Peter Forsell, Menzingen, Switzerland

[73] Assignee: Kirk Promotions Limited, St. Johns, United Kingdom

[21] Appl. No.: 09/106,142

[22] Filed: Jun. 29, 1998

[51] Int. Cl.[7] .................................................. A61B 17/08
[52] U.S. Cl. ............................................................ 606/157
[58] Field of Search ..................................... 606/157, 151, 606/201–203, 213, 228; 128/898, 899

[56] References Cited

U.S. PATENT DOCUMENTS

| | | |
|---|---|---|
| 3,875,928 | 4/1975 | Angelchik . |
| 4,592,339 | 6/1986 | Kuzmak et al. . |
| 5,160,338 | 11/1992 | Vincent . |
| 5,449,368 | 9/1995 | Kuzmak ................................. 606/157 |
| 5,771,903 | 6/1998 | Jakobsson ............................... 606/151 |

FOREIGN PATENT DOCUMENTS

| | | |
|---|---|---|
| 906-526 | 2/1982 | U.S.S.R. . |

*Primary Examiner*—Michael Buiz
*Assistant Examiner*—Vikki Trinh
*Attorney, Agent, or Firm*—Burns, Doane, Swecker & Mathis, L.L.P.

[57] ABSTRACT

A surgical method for reducing the food intake of a patient includes the steps of dissecting the lower part of the Esophagus, applying a band to form a loop around the Esophagus, displacing an upper part of the stomach through the loop, so as to form a small pouch above said band in connection with the Esophagus, and suturing the upper part to the stomach portion situated below the band loop, thereby tunnelating said band. A device useful in performing this method includes an elongated band having a flexible substantially non-expansible outer wall and a flexible and expansible inner wall joined to the outer wall to form an expansible closed cavity. The band has a length such that, when its ends are joined to each other, it forms a loop around the Esophagus, while permitting an upper part of the stomach to be introduced through the opening of the loop. A conduit extends between the band's cavity and an injection port. By injecting fluid through the port, the inner wall in the band loop may be inwardly expanded from adjacent to the outer wall to substantially completely obstruct the loop opening. The band further has a wider portion intended to bear against the posterior side of the Esophagus.

46 Claims, 7 Drawing Sheets

SURGICAL METHOD AND DEVICE FOR REDUCING THE FOOD INTAKE OF PATIENT

BACKGROUND OF THE INVENTION

1. Field of the Invention

The present invention relates to a surgical method for reducing the food intake of a patient in need of such a treatment. More specifically, the invention relates to a food intake restriction device and a surgical method of implanting the device in a patent.

2. Brief Description of the Related Art

In the early 1980s, surgical procedures to treat overweight patients were often carried out by placing a band around the stomach, which formed a restriction, thereby preventing food from passing downwards, or more correctly reducing the speed and the amount of food being eaten. After a few years of use of the new surgical method it became evident that it was very difficult to apply the band with an appropriate tightness—if the band was too tight around the stomach, patients were affected by vomiting attacks. Alternatively, if the band was too loose, the opening between the upper and lower parts of the stomach became too large, resulting in the eating or the weight problems being unaffected. Unfortunately, many of these operations therefore resulted in failure.

The solution to this problem was to provide a band having an inflatable balloon on the inside thereof, like a blood pressure cuff. This balloon could be connected to an injection port, making it possible to change the inside diameter (the "stoma diameter") of the band after the operation. In this way, if after operation the band was found to be too tight, it was possible to drain off some fluid through the injection port. This procedure increased the opening of the band loop, resulting in a larger restriction between the upper and lower parts of the stomach. On the other hand, if patients did not lose weight, it was possible to inject fluid through the injection port, thereby narrowing the restriction between the upper and lower parts of the stomach. This operation was clearly better than the earlier method, but unfortunately this operation was not without problems. Namely, there existed two main difficulties.

First, the loop band continued to have a tendency to dislocate downwards towards the lower part of the stomach. This could be prevented by suturing the lower part of the stomach to the upper part of the stomach (called "tunneling") to prevent the band from dislocating downwards towards the major curvature of the stomach. However, sometimes these sutures ruptured, thus negatively affecting a desired long term weight loss.

The second difficulty, revealed by recent research, was that the upper part of the stomach rapidly increased in size, up to approximately ten times its original size, resulting in less weight reduction, because the effective size of the stomach was not reduced.

The most frequently used surgical method during this period was vertical-banded gastroplasty ("VBG"). In this operation, holes through both the back and front wall of the stomach were made with a two-row suture instrument. With another suture instrument a four row steel suture was made from these holes up to the angle of his. The smaller upper part of the stomach then functions as a prolongation of the esophagus. After this step a band was inserted through the hole and applied around the minor side of the stomach, the ends of the band being sutured to each other to form a closed band loop. This operation is not reversible. In a large study carried out in the United States by Mason, including more than 1000 patients, 14% of the patients required a second operation. The weight reduction resulting from this technique was by no means satisfactory.

Normally, when either the gastric band operation or the VBG operation is performed, the bursa omentalis between the lower part of the stomach and the colon is opened. A hole in the bursa omentalis is made under the stomach. It is then possible to operate from both sides of the stomach, i.e., both from the interior and the posterior side. In gastric banding, two holes on the minor and major side of the stomach are made. In VBG, where holes are made through both the back and front walls of the stomach using a two row suture instrument, penetration of the bursa omentalis is also required.

The upper part of the stomach wall is adherent to the underlying tissue. There is also a blood vessel—gastrica superior—quite high up, close to the stomach and coming up on the minor side of the stomach wall. Close to this blood vessel there is also a fibrotic band of fascia tissue extending from the stomach to the liver. In the gastric banding procedure, the band is typically placed below both this blood vessel and the fibrotic band and over through the fundus on the major side of the stomach. Because of the adherence of the stomach wall on the underside, the gastric band can not be localized higher up, when it is tightened around the stomach. When this operation is carried out, the stomach portion situated above the band is pulled downwards under the band and the stomach wall under the band is sutured to the stomach wall above the band thereby providing a tunnel for the band, preventing it from being dislocated downwardly and the same time making the size of the upper part of the stomach (the pouch volume) sufficiently small. If the stomach portion is not pulled downwardly, the pouch will be too large to be effective. But this measure also implies a pretensioning of the stomach portion, which results in this portion rapidly moving upward if the sutures rupture, which in turn results in a pouch volume that is undesirably large to affect sufficient weight loss in the patent as a consequence.

Normally, according to studies by the present inventors, the pouch volume initially will enlarge. It has thus been considered to be an absolute necessity that the tunneling sutures do not rupture, so that the small pouch volume may be maintained over the long term. The main problem however, is that even if the gastric band does not dislocate, the pouch volume nonetheless rapidly increases in size during the first year after the operation. These studies show that the average size of the upper gastric pouch increases up to ten times its original volume.

SUMMARY OF THE INVENTION

A major object of the invention is to provide a simple reliable substantially non-pressurized food intake restriction device for reducing the food intake of a patient.

Another object of the invention is to provide a new surgical method for reducing the food intake of a patient which is simpler and provides for a better long-term result with fewer postoperative complications than prior art methods.

In accordance with a first aspect of the invention, a food intake restriction device according to a first embodiment is provided for forming a food intake restriction above the bursa omentalis of a patient, comprising a band having an elongated, bendable, substantially non-expansible supporting outer wall and an elongated flexible inner wall joined to said outer supporting wall to form a closed expansible cavity, means for forming a loop of the band defining a restriction opening, the flexible inner wall being substantially broader than the supporting outer wall, and fluid supply means for adding fluid to and withdrawing fluid from said cavity to expand the flexible inner wall to decrease the size of said restriction opening and deflate the flexible inner wall to increase the size of said restriction opening. The substantially broader flexible inner wall protects efficiently the esophagus and cardia region from the relatively hard non-expansible supporting outer wall and the surface pressure exerted by the band against the esophagus and cardia region will be reduced, thereby diminishing the stress per unit area by the food intake restriction. This gives the important advantage that the risk of the band hurting and migrating through the wall of the esophagus or stomach will be decreased.

The lateral extension of the elongated inner wall in a fully inflated state is suitably more than 20 mm and less than 40 mm, whereas the relative narrow supporting outer wall usually is about 13 mm broad. The elongated inner wall may comprise a portion wider than the rest of said inner wall, suitably in the middle of said inner wall.

The inner flexible wall is advantageously designed to form a row of bulges along the band, when said cavity is at least partly filled with fluid. As a result, the inner wall will not create any creases when the band is inflated and forms a loop, but expose smooth surfaces on said bulges to abut the esophagus, the cardia region and the stomach. This bulge-design of the inner wall still permits the band to be inflated under a pressure in said cavity which is substantially equal to the ambient pressure, which eliminates the risk of fluid migrating through the outer and inner walls of the band.

In accordance with the first aspect of the invention, a food intake restriction device according to a second embodiment is provided for forming a stoma opening in the stomach or esophagus of a patient, comprising a band consisting of an elongated tubing having a pliable circumferential wall of a homogeneous material, said tubing forming a closed cavity, means for forming a loop of the band defining a restriction opening, and fluid distribution means for adding fluid to and withdrawing fluid from said cavity to adjust the volume of said cavity and the size of said restriction opening. As a result, the band lacks any hard supporting outer wall that might injure the esophagus and the stomach which is of particular advantage when the band is encircled by stomach wall portions because of tunneling sutures. To achieve the necessary adjustment of the size of the restriction opening, the tubing is simply designed broad enough to expand sufficiently from a flattened state radially inwardly of the loop. Besides, a broad tubing is beneficial with regard to the large surface area of the tubing that will contact the esophagus and the stomach.

The thickness of the circumferential wall of the tubing may suitably vary, preferably continuously, in the circumferential direction, so that two opposite axially extending portions of the circumferential wall differ in thickness. As a result, a relatively greater inward expansion of the tubing is achieved when the band inflates. The thinner one of said two opposite axially extending portions may suitably be designed to form a row of bulges along the band, when said cavity is at least partly filled with fluid. This gives the advantage that the formation of creases on the inner side of the tubing as the band is bent into a loop is avoided.

In accordance with the first aspect of the invention, a food intake restriction device according to a third embodiment is provided for forming a stoma opening in the stomach or esophagus of a patient, comprising an extensible band consisting of an elongated tubing having a circumferential wall of an elastic material, said tubing forming a closed cavity, means for forming a loop of the band defining a restriction opening, and fluid distribution means for adding fluid to and withdrawing fluid from said cavity to adjust the volume of said cavity and the size of said restriction opening. As a result, the extensible band is able to yield longitudinally to permit accidental large pieces of food to pass through the restriction opening. Furthermore, the elastic circumferential wall of the band is able to yield radially under the influences of dynamic movements of the stomach, i.e. the stomach has a certain freedom to move where it is in contact with the band, which significantly reduces the risk of the band injuring or migrating through the stomach wall. If the stomach wall were prevented from moving along the region where the band contacts the stomach, the stomach wall would became thinner over time, which dramatically increases the risk of the band penetrating the stomach wall.

The thickness of the circumferential elastic wall of the tubing may suitably vary, preferably continuously, in the circumferential direction, so that two opposite axially extending portions of the circumferential wall differ in thickness, whereby a relatively greater inward expansion of the tubing is achieved when the band inflates, if the thinner portion is located on the inner side of the band loop. Alternatively, or in combination with varying wall thickness, the same result is achieved by designing said two axially extending wall portions with different elasticity, whereby the more elastic portion is located on the inner side of the band loop.

Advantageously, one of said two opposite axially extending portions of the circumferential elastic wall, which is intended to form the inner side of the band loop, may be pretensioned or alternatively, may be designed to form a row of bulges along the band, when said cavity is at least partly filled with fluid, whereby the formation of creases on the inner side of the tubing as the band is bent into a loop is avoided.

In accordance with a second aspect of the invention, a surgical method is provided for reducing the food intake of a patient by the use of a food intake restriction device, which includes a flexible band having a closed expansible cavity, and fluid supply means for adding fluid to and withdrawing fluid from said cavity, the method comprising the steps of dissecting at least a part of a region of the cardia of the patient, said region consisting of the lower part of the esophagus, the cardia and a proximate part of the uppermost portion of the stomach that is adherent to the underlying tissue, so that a distal part of said uppermost portion of the stomach remains adherent to the underlying tissue, applying said band to form a loop around said dissected part of a region of the cardia, and displacing an anterior upper part of the stomach wall through said loop, thereby forming a small pouch of the stomach above said band. This method permits that a very small pouch for food may be shaped in a controlled manner.

The expression "a distal part" is meant to include a part of the uppermost portion of the stomach adherent to the underlying tissue as seen in the circumferential direction of the stomach. For example, a distal posterior part of the uppermost portion of the stomach on the left side of the patient may remain adherent to the underlying tissue.

Alternatively, the surgical method may comprise dissecting the lower part of the esophagus and at least a part of a region of the cardia of the patient, wherein said region consists of the cardia and said proximate part of the uppermost portion of the stomach that is adherent to the underlying tissue, so that a distal part of said uppermost portion of the stomach remains adherent to the underlying tissue. This alternative method gives the advantage that, as the pouch of the stomach increases in size after the surgery, the band is able to adjust its size and its position along the dissected part of said region of the cardia.

In accordance with a third aspect of the invention, a method is provided for laparascopically implanting a food intake restriction device including a band, the method comprising insufflating the abdomen of a patient to form a pneumoperitoneum, introducing at least one laparascopic trocar into the abdomen, dissecting by means of a dissection tool inserted through the laparascopic trocar at least a part of a region of the cardia of the patient, said region consisting of the lower part of the esophagus, the cardia and a proximate part of the uppermost portion of the stomach that is adherent to the underlying tissue, so that a distal part of said uppermost portion of the stomach remains adherent to the underlying tissue, introducing said band into the abdomen, operating a tool through the laparascopic trocars to pull said band around said dissected part of a region of the cardia so that said band extends in a loop, fixing said band to permanently extend in said loop, and displacing an anterior upper part of the stomach wall through said loop of said band, thereby forming a small pouch of the stomach above said band.

Alternatively, the laparascopic method may comprise dissecting the lower part of the esophagus and at least a part of a region of the cardia of the patient, wherein said region consists of the cardia and said proximate part of the uppermost portion of the stomach that is adherent to the underlying tissue, so that a distal part of said uppermost portion of the stomach remains adherent to the underlying tissue, and operating said tool through the trocar to pull said band around said dissected lower part of the esophagus so that said band extends in a loop.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DETAILED DESCRIPTION OF THE PREFERRED EMBODIMENTS

Figure 1:
FIG. 1 is a perspective view which schematically shows the device of the present invention in place on the stomach and esophagus following surgical implantation.

Referring to the drawing figures, like reference numerals designate identical or corresponding elements throughout the several figures.

A first exemplary embodiment of a food intake restriction device in accordance with the present invention will now be described with reference to FIG. 2. The device includes a band 11, having a supporting elongated outer wall 13 of a substantially non-expansible and flexible material. Wall 13 is preferably made of a reinforced plastic material and has such a flexibility that it could be bent to form a closed loop defining a restriction opening. The band 11 has a length enabling the closed loop of the band to be formed around one of the lower part of the esophagus, the cardia, and the esophagus-cardia junction, and also enabling an anterior upper part of the stomach wall to be pulled through the closed loop to form a small pouch 5 (see FIG. 1) of the stomach. The ends 15, 17 of the outer wall 13 may be joined to each other, e.g., by suturing, by a snap-lock connection, or by any other suitable joining means, as will be readily apparent to one of ordinary skill in the art.

Band 11 preferably has an inner wall 19 made of an expansible material, preferably an elastic, soft plastic material or the like. Inner wall 19 is joined to the outer wall 13, e.g., by gluing heat-sealing, solvent bonding, mechanical means such as riveting or suturing, or any other suitable means as will be readily apparent to one of ordinary skill in the art, thereby providing an expansible cavity 26 between the walls 13, 19. In an alternative embodiment the flexible inner wall 19 forms a tubular balloon connected (e.g., glued or heat-sealed) to the outer wall 13, so that the outer wall abuts the outer surface of the tubular balloon. The width or lateral extent of the elongated inner wall 19 in a fully inflated state is preferably between about 20 mm and about 40 mm, whereas the width or lateral extent of the outer wall 13 preferably is about 13 mm.

A fluid supply device is provided for adding fluid to and withdrawing fluid from cavity 26 to expand the flexible inner wall 19 to decrease the size of the restriction opening and deflate the flexible inner wall 19 to increase the size of the restriction opening. According to a first exemplary embodiment of the fluid supply device, an injection port 23 and a flexible conduit 21 fluidly connect the injection port 23 to cavity 26. The injection port 23 is implanted in an easily accessible region on the patient, preferably placed subcutaneously against the lower part of the sternum 8 (see FIG. 1), thereby providing a support for the injection port during fluid injection. The flexible conduit 21, which suitably is made of a tube of silicone rubber or other flexible biocompatible material, has a length such that when the band 11 is applied on the stomach and the injection port 23 is implanted against the sternum 8, the conduit 21 extends downwardly from both the band 11 and the sternum 8 to form an open loop therebetween.

The inner wall of the band 19 may be inwardly expanded from adjacent the outer wall 13 to such an extent that when a band loop has been formed, the opening of the loop will be substantially obstructed. In a preferred embodiment, as when used in the surgical method of the present invention, the unexpanded loop has an inner diameter of approximately 35 mm.

In a preferred embodiment the band 11 varies in width along its long axis, thereby providing a support portion 25 approximately in the middle of the band 11 with a greater area intended to rest against the esophagus 3 (or, alternatively, on the posterior part of the esophagus-cardia junction, or on the posterior surface of the cardia). In this way the surface pressure against the esophagus 3 wall (or alternatively, on the posterior part of the esophagus-cardia junction, or on the posterior surface of the cardia) will be reduced, thereby diminishing the stress per unit area placed on the esophagus 3 wall (or alternatively, on the posterior part of the esophagus-cardia junction, or on the posterior surface of the cardia) by the band 11.

The wide range of adjustment of the cavity 26 or the inner wall 19 is a very important feature of the band 11 for accomplishing a satisfying long term result of the method of the invention.

For use in the method of the present invention, see FIG. 1, the band 11 loop is initially disposed around the esophagus 3 (or, alternatively, on the posterior part of the esophagus-cardia junction, or on the posterior surface of the cardia), whereupon the upper part of the stomach 1 is pulled up through the band loop and then sutured to a portion of the stomach 1 situated below the restriction, thereby forming the pouch 5, and tunnellating the band 11. This pouch 5 preferably has a very small initial volume, e.g., about 7 ml. If the loop were directly tightened to its final size in association with the operation, the pouch volume would be too small to give the patient sufficient nutrition immediately after the operation. However, the pouch 5 will expand in the course of time, normally up to ten times its original size after about a year. Therefore, in order to forestall potential malnutrition problems the opening of the loop is initially adjusted to have its maximum size just after the operation. As time passes, the pouch 5 will expand, and the loop opening may be correspondingly reduced without serious consequences for the patient. The reduction in the size of the band loop is accomplished by injecting through the injection port 23 connected to the band 11 an appropriate amount of fluid into the cavity of the band loop. This adjustment may be carried out as frequently as necessary in order to follow the expansion of the pouch 5.

At the end of the expansion of the pouch 5, typically after about one year, the loop opening will have been reduced to its final size. The total process thus may be completed with a smooth, stepwise reduction of the loop opening, and without appreciable problems for the patient.

It should be noted that the device could be varied in different ways. For example, the fluid might be a gas, but preferably it is a liquid, preferably an oil or an isotonic salt solution. It should further be evident that all components of the device are made of biocompatible materials.

Figure 3:
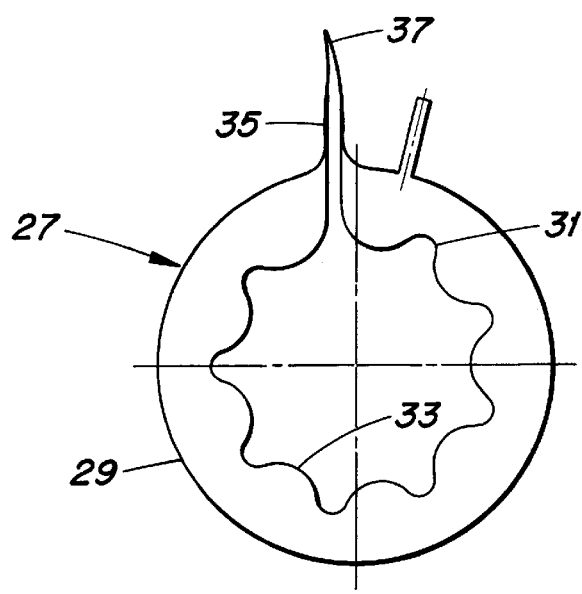
FIG. 3 is a cross-section through a band of a second embodiment of a device in accordance with the present invention.

FIG. 3 illustrates a second exemplary embodiment of a band in accordance with the present invention. A non-extensible band 27 includes an outer non-extensible supporting wall 29 and an inner flexible wall 31 designed to form a row of protuberances or bulges 33, preferably including at least three bulges 33, and more preferably nine bulges 33, along the inner surface of band 27. Bulges 33 act to bear against that portion of the anatomy around which band 27 is placed, to hold the band in place. Providing band 27 with at least three bulges 33 stabilizes the band in a single plane, as will be readily apparent to one of ordinary skill in the art. The bulges 33 are completely extended and adjacent bulges 33 are spaced apart from each other when the cavity of the band 27 is filled with fluid. The band 27 is provided with end flaps 35 and 37, which can be joined together, so that the band 27 forms a closed loop with the bulges 33 directed radially inwards to softly abut against the esophagus and stomach of a patient.

Figure 4:
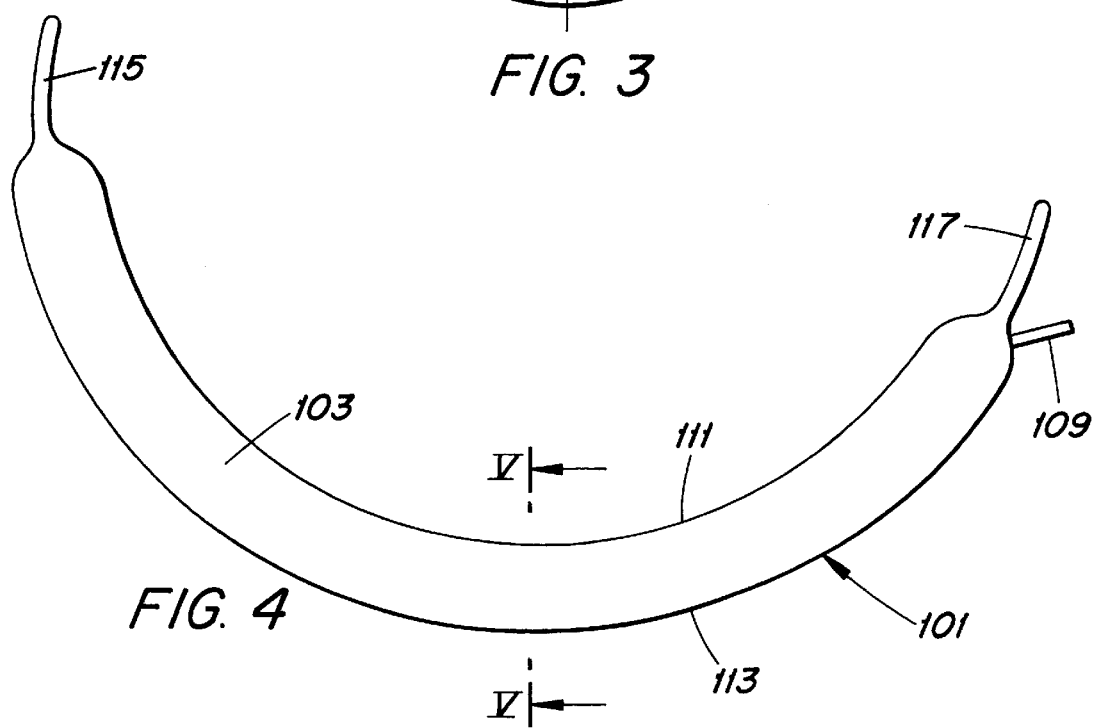
FIG. 4 is a view of a band of a third embodiment of the device in accordance with the present invention.
Figure 5:
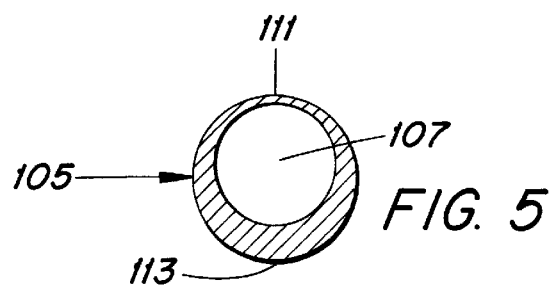
FIG. 5 is a cross-section along the line V—V in FIG. 4.

FIG. 4 illustrates a third exemplary embodiment of a band in accordance with the present invention for forming a stoma opening in the stomach or esophagus of a patient. The extensible band 101 includes an elongated tubing 103 having a circumferential wall 105 of an elastic material. The tubing 103 forms a closed cavity 107 (see FIG. 5) with an inlet 109 for the supply of a fluid, preferably liquid into the cavity. The circumferential wall 105 has a relative thin axially extending portion 111 and a relatively thick axially extending portion 113 situated opposite thereof. The band 101 is provided with two end flaps 115 and 117, similar to flaps 35, 37 described above. In the context of describing exemplary embodiments of the present invention, the term "axially," when used to describe a band of the food intake restriction device, refers to the direction between the respective ends of a band, including when the band assumes a configuration which is not linear.

Alternatively, the circumferential wall 105 of the tubing 103 may be of a pliable and homogeneous material and not necessarily be elastic.

Figure 6:
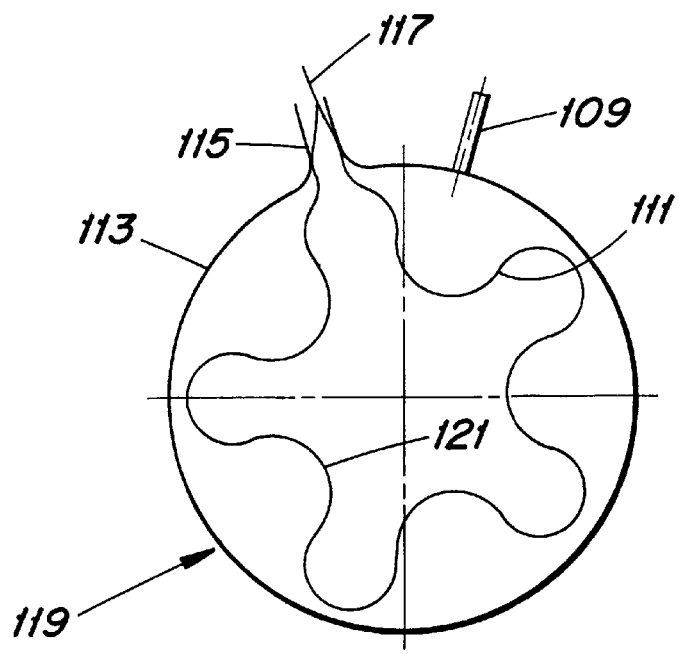
FIG. 6 is a cross-section through a fourth embodiment of a band in accordance with the present invention and forming a loop.

FIG. 6 illustrates a fourth exemplary embodiment of a band in accordance with the present invention. Band 119 has components similar to those of the band 101 shown in FIG. 4, except that the thin portion 111 of the circumferential wall 105 is designed differently. The two end flaps 115 and 117 of the band 119 are joined to each other, so that the band 119 forms a loop with the thin portion 111 of the wall 105 extending along the inner portions of the loop and, consequently, with the thick portion 113 extending along the outer portions of the loop. The thin portion 111 is designed to form a row of bulges 121 including at least three bulges 121, and preferably five bulges 121, along the band 119. The bulges 121 are completely extended and adjacent bulges 121 are spaced apart from each other when the cavity 107 of the band 119 is filled with fluid.

Figure 7:
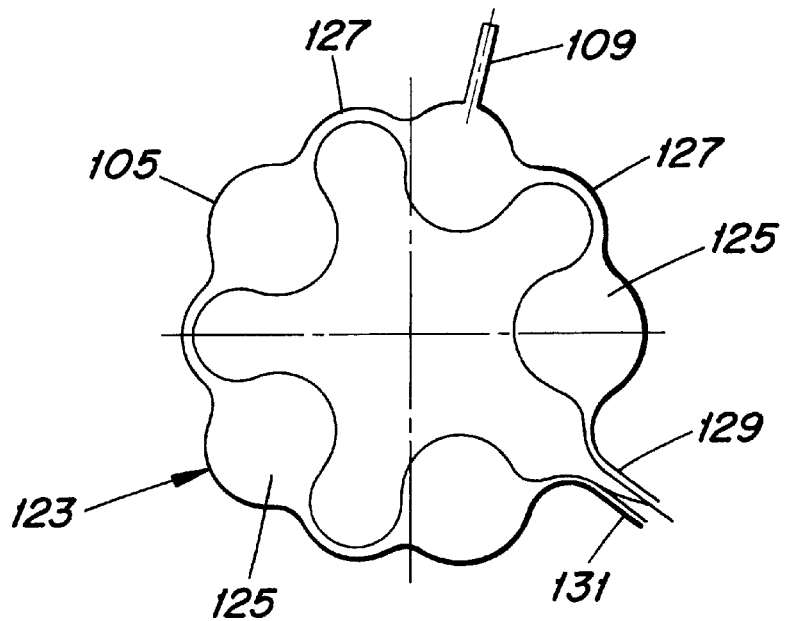
FIG. 7 is a cross-section through a fifth embodiment of a band in accordance with the present invention and forming a loop.

FIG. 7 illustrates a fifth exemplary embodiment of a band in accordance with the present invention, in which a band 123 has components similar to those of the band 119, except that the circumferential wall 105 is uniformly thick and designed to form a number of interconnected but spaced apart spherical portions 125, here five portions 125, along the band 123. Portions 125 are fluidly interconnected by non-extensible portions 127. Band 123 also includes flaps 129, 131, similar to flaps 115, 117 described above.

In the surgical method of the present invention, the bursa omentalis is not opened. After the penetration of the abdominal wall, the left lobe of the liver is released from the diaphragm muscle. In this area there is only a fibrotic connection without any blood vessels.

Figure 2:
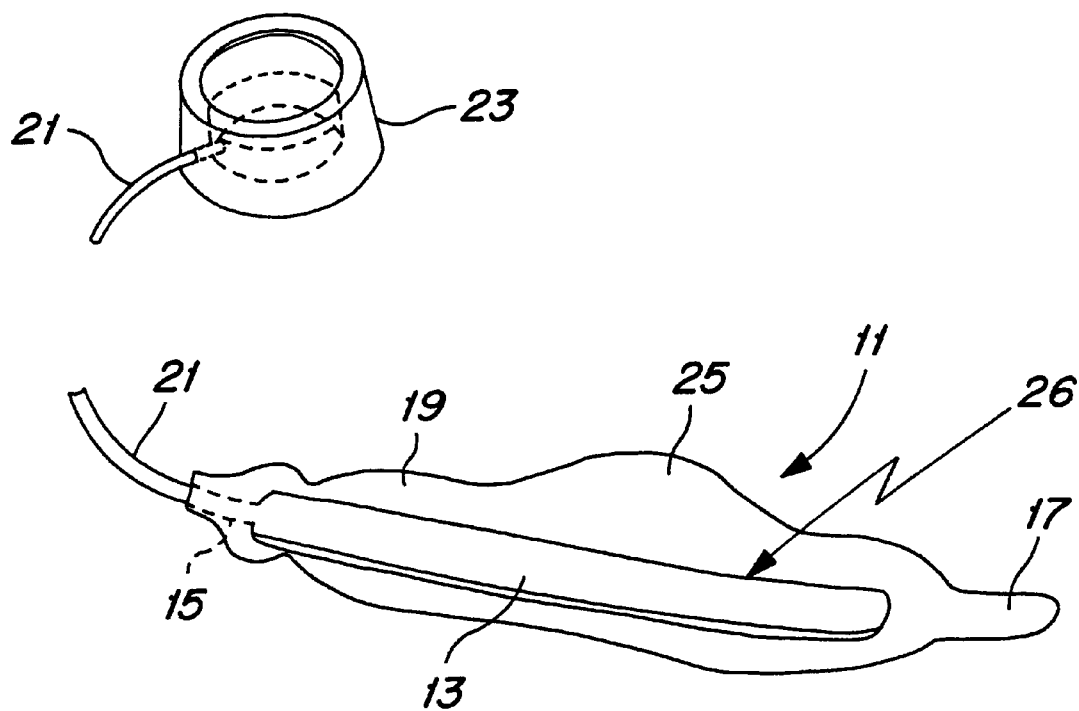
FIG. 2 presents a schematic perspective view of a first embodiment of device in accordance with the present invention.

The following description of the surgical method of the present invention makes reference to FIG. 1. After release of the left liver lobe, the lower part of the esophagus 3 easily can be seen. The lower part of the esophagus 3 is then released and a band of a food intake restriction device of the present invention is then applied around the lower part of the esophagus 3. In an alternative embodiment, the band may be placed slightly lower, at the junction between the esophagus and the cardiac portion of the stomach ("cardia"), or lower still, around the cardia. The two ends of the band are then sutured to each other to form a loop (the function of the loop will be explained below). The most upper part of the anterior stomach 1 wall is pulled up inside the band loop and then the small part of the stomach 1 wall forming a pouch 5 above the band is sutured to the lower part of the stomach situated below the band, which is tunnellated by a row of sutures 7 at the anterior wall. The band is now in a very stable position, resting on the posterior part of the esophagus 3 (or alternatively, on the posterior part of the esophagus-cardia junction, or on the posterior surface of the cardia). Due to the adherence of the upper part of the stomach 1 to the underlying tissue, the lower part of the esophagus and the upper part of the cardia are very stable in this area. Thus, there is no possibility that the band will dislocate downwardly. When the most upper part of the anterior stomach wall is pulled through the band and the tunneling sutures 7 are made, the posterior part of the band will be situated around the esophagus 3 (or alternatively, on the posterior part of the esophagus-cardia junction, or on the posterior surface of the cardia). The anterior part of the band will preferably be placed as much as 2 cm below the cardia.

The surgical method of the present invention provides the following advantages over prior art methods:

1. The band has a very stable position. There is no risk for further dislocation of the band downwards towards the stomach 1, thus ensuring good long term results.

2. The tunneling sutures 7 are not critical for achieving good results with this method. They only facilitate in the beginning the expansion of the very small food pouch 5.

3. The surgical method is much easier with less risks and less operating time than in prior art methods.

4. A very small upper pouch 5 may be formed. This is particularly important, since the pouch can be expected to expand about ten times in size in the first postoperative year. A small pouch 5 volume predicts a good long term result.

5. The method of the present invention allows for a wide range of adjustment of the stoma diameter, so that the stoma opening may be decreased during a long period of time concurrently with the expansion of the pouch.

6. The risk of the band injuring the esophagus and/or the stomach is substantially reduced. Later migration of the band into the wall of the esophagus and/or the stomach is avoided.

In the laparascopic surgical method of the invention, a number of trocars are used for various surgical instruments. Thus, an optic trocar is placed on the line between the umbilicus and xiphold, at the transition of the middle and lower third of this distance. An incision is made and the trocar is inserted at an angle of approx. 30°–35° upwards and 15° towards the right (from the operator's point of view). A liver retractor is placed on the subcostal right side of the patient, lateral to the medioclavicular line. The trocar for the liver retractor is inserted towards the left of the upper abdomen. A babcok is placed on the subcostal left side of the patient, lateral to the medioclavicular line. The trocar for the babcok is inserted at a steep upward angle, so that the trocar aims towards the hiatus.

A trocar for the right instrument (from the operator's point of view) is placed between the optic and the babcok trocars, 3–4 cm cranial from a horizontal line or the babcok level, and is inserted at an angle of approximately 40° in direction of the cranium following a straight line parallel to the body axis (aiming towards the hiatus). A trocar for the left instrument (from the operator's point of view) is placed half way between the optic and liver retractor trocars, 2–3 cm cranial from a horizontal line passing through the liver retractor, and is inserted at an angle of approximately 35° in direction of the cranium aiming at the hiatus to make a perforation through the ligamentum falciforme. A 15–20 mm trocar is inserted into the medium axillary line ten cm below the costal margin.

Figure 8:
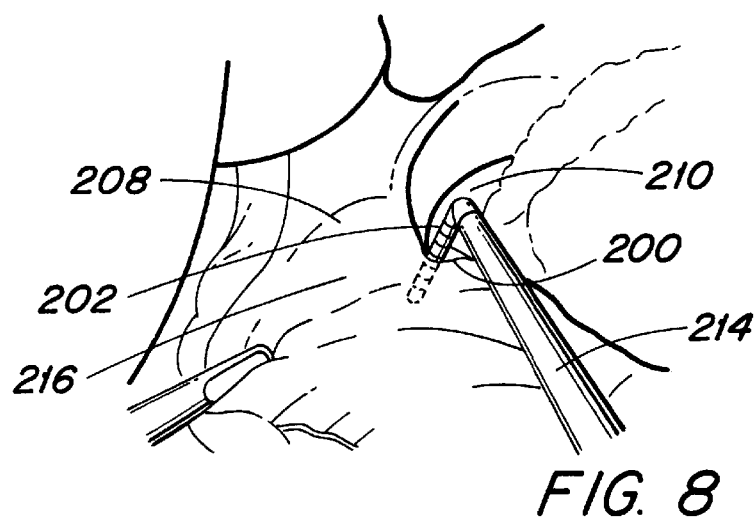
FIGS. 8–13 illustrate steps of a surgical method in accordance with the present invention.

At the angle of his the gastrophrenic ligament is dissected in the following manner, see FIG. 8. The dissection is begun with the isolation of the left crus 200 and the creation of an opening 202 into the avascular part of the gastrophrenic ligament, just proximal to the first short gastric vessel, between the distal esophagus 208 and the upper pole of the spleen 210. The gastophrenic ligament is incised by using an electric hook or endo-scissors. Further dissection of the gastophrenic ligament is carried out by using a flexible, blunt, smooth tool 214, such as the GoldFinger, marketed by Obtech Medical AG (ZUG, Switzerland), and should be performed between the left crus 200 and the cardia 216, as far down (distal) as possible.

Figure 9:
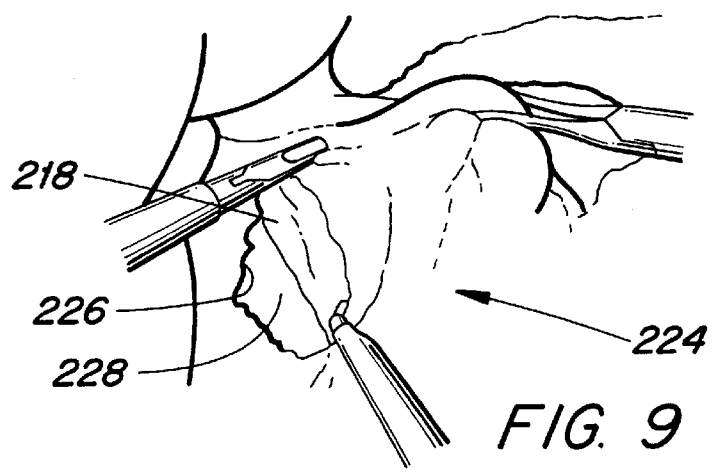
Figure 10:
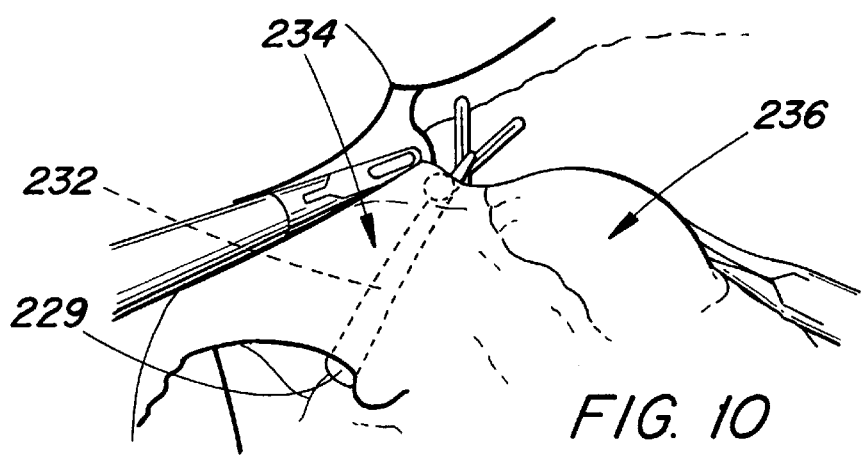

The lesser curvature is dissected in the following manner. Dissection is performed high up at the lesser curvature, at the bottom of the right crus 218 but above the arteria gastrica sinistra. Placing the band 11 of a food intake restriction device in accordance with the present invention above the gastrica sinistra will make it possible to enclose all the fat on the lesser curvature within the loop of the band, thus eliminating time-consuming dissection. This measure will also ensure a stable placement of the band. There is no cause for concern about interfering with the vagus nerve. The band of the present invention is a zero pressure system when filled with the recommended amount of fluid. The omentum minus 224 is dissected in the pars flaccida 226 and the caudate lobe 228 is delineated. An opening 229 is created in the retroperitoneum at the bottom of the diaphragmatic crus, see FIG. 9, and a passage 232 is dissected behind the esophagus 234, see FIG. 10. Dissection should be approximately 1.0 cm away (distal) from the right crus 218.

Figure 11:
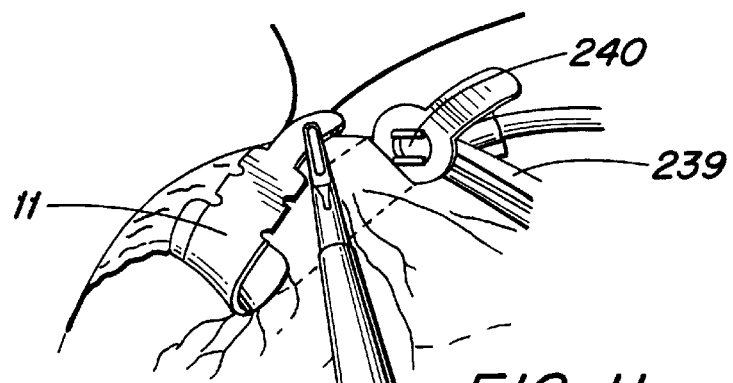

The application of the band 11 in a collapsed flattened state is carried out in the following manner. Two pieces of thread, such as an Ethibond 2-0 or the like, are inserted through a small hole at the top of the flap, on the extremity without the flexible inner wall. The pieces of thread are tied into two loops, one loop as a spare. These thread loops will be useful for pulling the band behind the esophagus 234 or the stomach 236. The band is inserted into the abdomen through the 15–20 mm trocar. A tool, such as the GoldFinger, is passed behind the esophagus 234 and is pushed back up through the opening made in the gastophrenic ligament, see FIG. 10. The thread loop is fixed in the distal slot of the GoldFinger tool and the band is placed so that the inflatable part is facing the gastric wall. The band can now easily be pulled around the back of the esophagus or the stomach, through the opening made on the lesser curvature, see FIG. 11.

The band is simply closed by inserting one flap through the other. While holding the band by its flap situated to the flexible inner wall, a Heys-type clamp 239 or grasping forceps is inserted through an aperture 240 at the base of the flap to grab hold of the other flap, which is pulled back through the opening far enough so that it rests in a self-locking position.

Figure 12:
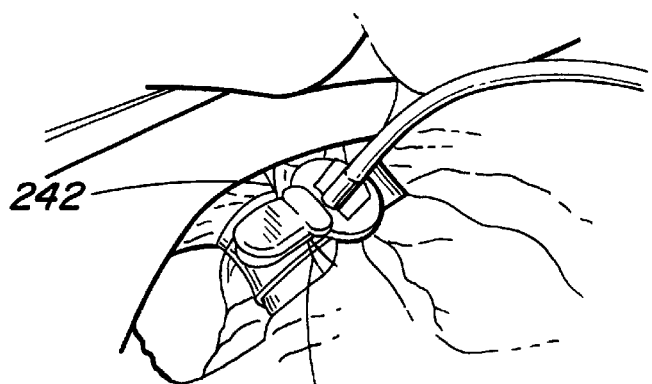

The band is secured by placing two non-resorbable suture knots 242 as close as possible to the base of the flaps, in and next to a small hole made for this purpose, see FIG. 12. Then, the flaps are moved round so that they rest on the side of the greater curvature. The anterior (distal) side of the band is placed lower than the posterior side of the band.

Figure 13:
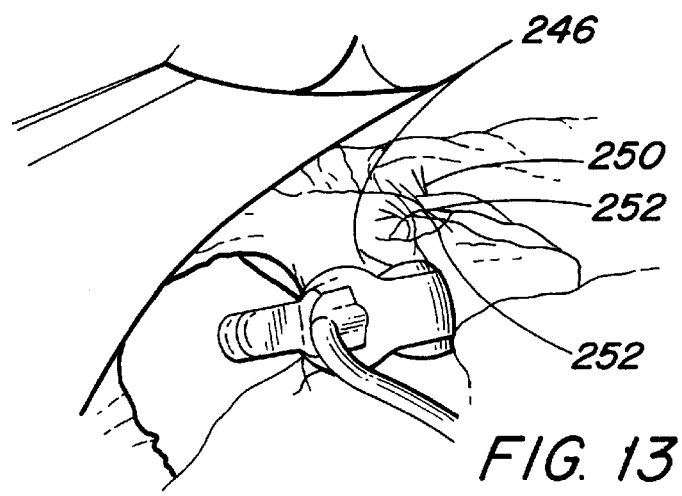

With the band pushed down towards the ventral side, a small pouch of the stomach, about the size of a third of a table tennis ball (e.g., about 1 mm diameter), is formed in the following manner. A catheter, e.g., a 36F gastroesophageal tube produced by Obtech Medical AG with a balloon that inflates on the ventral side only, is introduced so that its balloon is facing the ventral side of the stomach and is positioned between the adjustable band and the cardia. The 36 F gastric tube's balloon is expanded to approximately 25 ml, in order to distend the stomach wall. A proximal gastric pouch 246 of about 10 ml of relaxed volume is created by pulling the band down 1–2 cm below the gastro-esophageal junction, leaving it higher at the back. Three to four non-resorbable sutures 250 (using 2-0 or 3-0 thread) are placed between the anterior layers of the stomach 252, just proximal and distal to the band. The stomach is grabbed fairly low below the band so that enough space is created for the flexible wall to expand when it is later filled with fluid, preferably liquid contrast medium, e.g., lopamiro (Astra Pharmaceuticals). The upper row of sutures 250 is placed approximately 2 cm below the cardia, slightly below the fatty pad which is normally present in the cardia region, see FIG. 13. The aim is to perform deep seromuscular sutures. At this point, the metal nozzle of the injection port 23 is pushed into the tube 21. The metal connector is pushed back over the flexible wall right up to the port. The metal connector includes a small hook which is securely fitted into a small indent visible on the rim of the port. The balloon is evacuated of all air via the port, using a Huber needle. The remaining tube is inserted down into the abdomen to form a loop therein. Once the port is secured against the sternum, the incision is closed with normal skin sutures.

Figure 14:
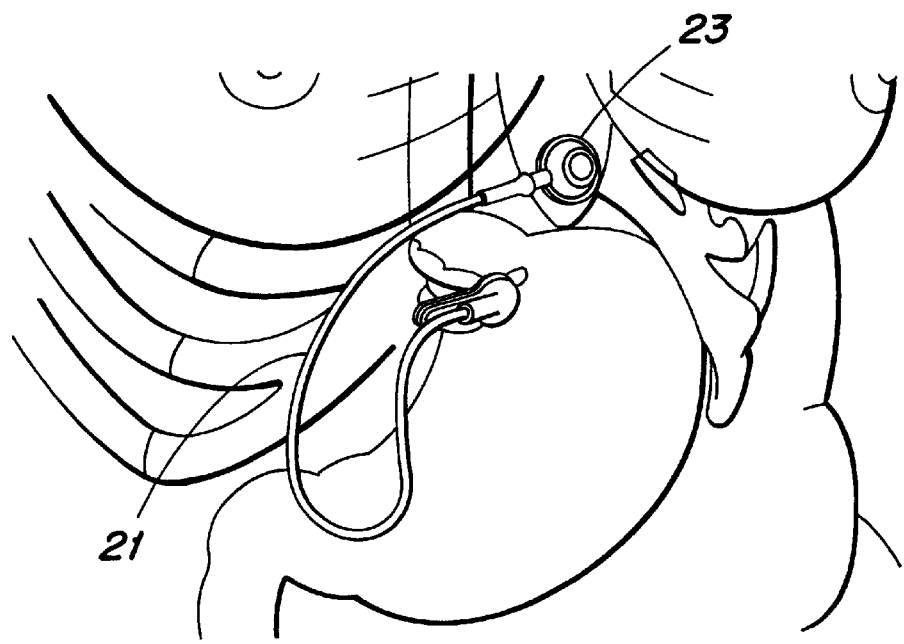
FIGS. 14 and 15 illustrate two different final positions of a device in accordance with the present invention implanted in a patient.
Figure 15:
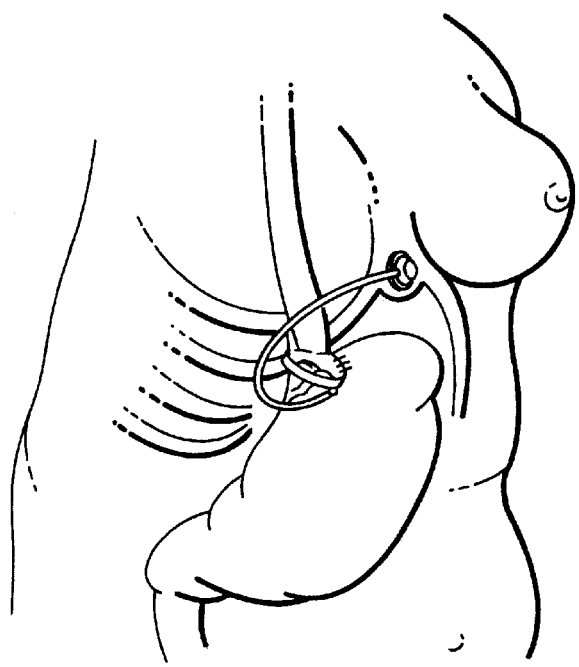

The final position of the food intake restriction device is illustrated in FIGS. 14 and 15.

The method of the invention provides for a stable positioning of the band much higher up, above the arteria gastrica sinistra, than in previous food intake restriction operations, which has proven to be of advantage with respect to the reoperating rate, which has been reduced dramatically. Moreover, the method of the invention does not require opening or removal of any part of the stomach or intestines, nor any altering of the natural anatomy. The patient recovers in a very short period. Normally the patient returns home the day after the treatment. The patient's weight loss results in the long term has proven excellent.

While the invention has been described in detail with reference to preferred embodiments thereof, it will be apparent to one skilled in the art that various changes can be made, and equivalents employed, without departing from the scope of the invention.

What is claimed is:

1. A food intake restriction device for forming a food intake restriction above the bursa omentalis of a patient, comprising:
   a band having an elongated, bendable supporting outer wall having a longitudinal length and which is substantially non-expansible in its longitudinal direction, and an elongated flexible inner wall joined to said outer supporting wall to form a closed expansible cavity, said flexible inner wall having a longitudinal length and forming a tubular balloon, said supporting outer wall abutting the outer surface of said tubular balloon,
   means for forming a loop of the band defining a restriction opening,
   the length of the flexible inner wall being substantially greater than the length of the supporting outer wall, and
   fluid supply means for adding fluid to and withdrawing fluid from said cavity to expand the flexible inner wall to decrease the size of said restriction opening and to deflate the flexible inner wall to increase the size of said restriction opening.

2. A food intake restriction device according to claim 1, wherein the lateral extension of the elongated inner wall in a fully inflated state is between 20 mm and 40 mm.

3. A food intake restriction device according to claim 1, wherein the elongated inner wall comprises a portion wider than the rest of said inner wall.

4. A food intake restriction device according to claim 3, wherein said wider portion of the inner wall is located centrally on said inner wall.

5. A food intake restriction device according to claim 1, wherein the inner flexible wall is designed to form a row of bulges along the band, when said cavity is at least partly filled with fluid.

6. A food intake restriction device according to claim 5, wherein the bulges of the flexible wall are spaced apart from one another.

7. A food intake restriction device for forming a stoma opening in the stomach or esophagus of a patient, comprising:
   a band consisting essentially of an elongated tubing having a pliable circumferential wall of a homogeneous material, said tubing forming a closed cavity,
   means for forming a loop of the band defining a restriction opening, and
   fluid distribution means for adding fluid to and withdrawing fluid from said cavity to adjust the volume of said cavity and the size of said restriction opening.

8. A food intake restriction device according to claim 7, wherein the thickness of the circumferential wall of the tubing is non-uniform along the circumference of said tubing.

9. A food intake restriction device according to claim 8, wherein the thickness of the circumferential wall of the tubing changes continuously along the circumference of said tubing.

10. A food intake restriction device according to claim 8, wherein two opposite axially extending portions of the circumferential wall differ in thickness.

11. A food intake restriction device according to claim 10, wherein the thinner one of said two opposite axially extending portions of the circumferential wall is designed to form a row of bulges along the band, when said cavity is at least partly filled with fluid.

12. A food intake restriction device according to claim 11, wherein the bulges of the flexible wall are spaced apart from one another.

13. A food intake restriction device for forming a stoma opening in the stomach or esophagus of a patient, comprising:
   a longitudinally extensible-band consisting essentially of an elongated tubing having a circumferential wall of an elastic material, said tubing forming a closed cavity,
   means for forming a loop of the band defining a restriction opening, and
   fluid distribution means for adding fluid to and withdrawing fluid from said cavity to adjust the volume of said cavity and the size of said restriction opening.

14. A food intake restriction device according to claim 13, wherein the thickness of the circumferential wall of the tubing is non-uniform along the circumference of said tubing.

15. A food intake restriction device according to claim 14, wherein the thickness of the circumferential wall of the tubing changes continuously along the circumference of said tubing.

16. A food intake restriction device according to claim 13, wherein two opposite axially extending portions of the circumferential wall have different elasticity.

17. A food intake restriction device according to claim 13, wherein two opposite axially extending portions of the circumferential wall differ in thickness.

18. A food intake restriction device according to claim 13, wherein one of two opposite axially extending portions of the circumferential wall, which forms said inner side of said band loop, is pretensioned, whereby the formation of creases on the inner side of said tubing as said band is bent into a loop is avoided.

19. A food intake restriction device according to claim 13, wherein one of two opposite axially extending portions of the circumferential wall is designed to form a row of bulges along the band, when said cavity is at least partly filled with fluid.

20. A food intake restriction device according to claim 19, wherein said bulges are spaced apart from one another.

21. A surgical method for reducing the food intake of a patient by the use of a food intake restriction device, which includes a flexible band having a closed expansible cavity, and fluid supply means for adding fluid to and withdrawing fluid from said cavity, the method comprising the steps of:

dissecting at least a part of a region of the cardia of the patient, said region selected from the group consisting of the cardia and a proximate part of the uppermost portion of the stomach that is adherent to the underlying tissue, so that a distal part of said uppermost portion of the stomach remains adherent to the underlying tissue;

applying said band to form a loop around said dissected part of a region of the cardia; and displacing an anterior upper part of the stomach wall through said loop, thereby forming a small pouch of the stomach above said band.

22. A surgical method according to claim 21 wherein said dissecting step includes dissecting the fat on the lesser curvature at the bottom of the right crus between the right crus and the arteria gastrica sinistra.

23. A surgical method according to claim 22 wherein said dissecting step includes opening the pars flaccida at the right side of said region of the cardia.

24. A surgical method according to claim 22 wherein said dissecting step includes dissecting at the angle of his.

25. A surgical method according to claim 21, wherein the anterior upper part of the stomach wall is displaced through said loop of the band so that the part of the band abutting the anterior stomach wall is lower than the posterior part of the band and positioned up to about two cm below the cardia.

26. A method for laparascopically implanting a food intake restriction device including a band, comprising:

insufflating the abdomen of a patient to form a pneumoperitoneum;

introducing at least one laparascopic trocar into the abdomen;

dissecting by means of a dissection tool inserted through the laparascopic trocar at least a part of a region of the cardia of the patient, said region selected from the group consisting of the lower part of the esophagus, the cardia, and a proximate part of the uppermost portion of the stomach that is adherent to the underlying tissue, so that a distal part of said uppermost portion of the stomach remains adherent to the underlying tissue;

introducing said band into the abdomen;

operating a tool through the laparascopic trocar to pull said band around said dissected part of a region of the cardia so that said band extends in a loop;

fixing said band to permanently extend in said loop; and displacing an anterior upper part of the stomach wall through said loop of said band, thereby forming a small pouch of the stomach above said band.

27. A surgical method according to claim 26 wherein said dissecting step includes dissecting the fat on the lesser curvature at the bottom of the right crus between the right crus and the arteria gastrica sinistra.

28. A surgical method according to claim 27 wherein said dissecting step includes opening the pars flaccida at the right side of said region of the cardia.

29. A surgical method according to claim 27 wherein said dissecting step includes dissecting at the angle of his.

30. A surgical method according to claim 26, wherein the anterior upper part of the stomach wall is displaced through said loop of the band so that the part of the band abutting the anterior stomach wall is lower than the posterior part of the band and positioned up to about two cm below the cardia.

31. A surgical method according to claim 26, wherein said region of the cardia extends from the esophagus about 3 cm above the cardia down to the bursa omentalis.

32. A method for laparoscopically implanting a food intake restriction device including a band, comprising:

insufflating the abdomen of the patient to form a pneumoperitoneum;

introducing at least one laparascopic trocar into the abdomen;

dissecting by means of a dissection tool inserted through the laparascopic trocar the lower part of the esophagus and at least a part of a region of the cardia of the patient, said region consisting of the cardia and a proximate part of the uppermost portion of the stomach that is adherent to the underlying tissue, so that a distal part of said uppermost portion of the stomach remains adherent to the underlying tissue;

introducing said band into the abdomen;

operating a tool through the trocar to pull said band around said dissected lower part of the esophagus so that said band extends in a loop;

fixing said band to permanently extend in said loop; and displacing an anterior upper part of the stomach wall through said loop of said band, thereby forming a small pouch of the stomach above the band, wherein the final position of said band is above the bursa omentalis.

33. A surgical method for reducing the food intake of a patient, comprising the steps of:

providing a food intake restriction device according to claim 1;

dissecting at least a part of a region of the cardia of the patient, said region selected from the group consisting of the lower part of the esophagus, the cardia, and a proximate part of the uppermost portion of the stomach that is adherent to the underlying tissue, so that a distal part of said uppermost portion of the stomach remains adherent to the underlying tissue;

applying the band of said food intake restriction device to form a loop around said dissected part of a region of the cardia; and displacing an anterior upper part of the stomach wall through said loop, thereby forming a small pouch of the stomach above said band.

34. A surgical method for reducing the food intake of a patient, comprising the steps of:
- providing a food intake restriction device according to claim 1;
- dissecting the lower part of the esophagus and at least a part of a region of the cardia of the patient, said region consisting essentially of the cardia and a proximate part of the uppermost portion of the stomach that is adherent to the underlying tissue, so that a distal part of said uppermost portion of the stomach remains adherent to the underlying tissue;
- applying said band of said food intake restriction device to form a loop around said dissected lower part of the esophagus; and
- displacing an anterior upper part of the stomach wall through said loop, thereby forming a small pouch of the stomach above said band;
- wherein the final position of said band is above the bursa omentalis.

35. A surgical method for reducing the food intake of a patient, comprising the steps of:
- providing a food intake restriction device according to claim 13,
- dissecting at least a part of a region of the cardia of the patient, said region selected from the group consisting of the lower part of the esophagus, the cardia, and a proximate part of the uppermost portion of the stomach that is adherent to the underlying tissue;
- applying the band of said food intake restriction device to form a loop around said dissected part of a region of the cardia; and
- displacing an anterior upper part of the stomach wall through said loop, thereby forming a small pouch of the stomach above said band.

36. A surgical method according to claim 35, wherein said dissecting step includes dissecting the fat on the lesser curvature at the bottom of the right crus between the right crus and the arteria gastrica sinistra.

37. A surgical method according to claim 36, wherein said dissecting step includes opening the pars flaccida at the right side of said region of the cardia.

38. A surgical method according to claim 36, wherein said dissecting step includes dissecting at the right angle of his.

39. A surgical method according to claim 35, wherein the anterior upper part of the stomach wall is displaced through said loop of the band so that the part of the band abutting the anterior stomach wall is lower than the posterior part of the band and positioned up to about two cm below the cardia.

40. A surgical method according to claim 35, wherein said region of the cardia extends from the esophagus about 3 cm above the cardia down to the bursa omentalis.

41. A surgical method for reducing the food intake of a patient, comprising the steps of:
- providing a food intake restriction device according to claim 13;
- dissecting the lower part of the esophagus and at least a part of a region of the cardia of the patient, said region consisting essentially of the cardia and a proximate part of the uppermost portion of the stomach that is adherent to the underlying tissue, so that a distal part of said uppermost portion of the stomach remains adherent to the underlying tissue;
- applying said band of said food intake restriction device to form a loop around said dissected lower part of the esophagus; and
- displacing an anterior upper part of the stomach wall through said loop, thereby forming a small pouch of the stomach above said band;
- wherein the final position of said band is above the bursa omentalis.

42. A surgical method according to claim 41, wherein said dissecting step includes dissecting the fat on the lesser curvature at the bottom of the right crus between the right crus and the arteria gastrica sinistra.

43. A surgical method according to claim 42, wherein said dissecting step includes opening the pars flaccida at the right side of said region of the cardia.

44. A surgical method according to claim 42, wherein said dissecting step includes dissecting at the angle of his.

45. A surgical method according to claim 41, wherein the anterior upper part of the stomach wall is displaced through said loop of the band so that the part of the band abutting the anterior stomach wall is lower than the posterior part of the band and positioned up to about two cm below the cardia.

46. A surgical method according to claim 41, wherein said region of the cardia extends from the esophagus about 3 cm above the cardia down to the bursa omentalis.

\* \* \* \* \*

UNITED STATES PATENT AND TRADEMARK OFFICE
CERTIFICATE OF CORRECTION

PATENT NO.      : 6,102,922                                              Page 1 of 1
DATED           : August 15, 2000
INVENTOR(S)     : Arne Jakobsson et al.

It is certified that error appears in the above-identified patent and that said Letters Patent is hereby corrected as shown below:

<u>Title page,</u>
After item "[22] Filed:  Jun. 29, 1998", insert
-- Related U.S. Application Data
[63] Continuation-in-part of ser. no. 08/532,357, filed Sep. 22, 1995, Pat. No. 5,771,903. --.

<u>Column 1,</u>
Before line 5, insert -- This is a continuation-in-part of U.S. application number 08/532,357, filed September 22, 1995, now U.S. Patent No. 5,771,903. --

Signed and Sealed this

Twenty-second Day of October, 2002

Attest:

Attesting Officer

JAMES E. ROGAN
Director of the United States Patent and Trademark Office